United States Patent [19]

Rosendal

[11] Patent Number: Plant 6,154

[45] Date of Patent: Apr. 19, 1988

[54] EXACUM NAMED BLUE ROSETTE

[75] Inventor: Erik Rosendal, Assens, Denmark

[73] Assignee: Nurserymen's Exchange, San Francisco, Calif.

[21] Appl. No.: 832,931

[22] Filed: Feb. 24, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Townsend and Townsend

[57] ABSTRACT

A new and distinct variety of Exacum plant characterized by semidouble flowers, floriferousness, blooming habits and the sterility of the flower. The normal stamens are petalloid and arranged incurved as a rosette in the center of the lavender-blue-violet flower. Plants can be propagated by asexual processes true to type. Rooting ability of the variety is excellent. The type of flower differs from that of the other known single cultivars.

1 Drawing Sheet

BACKGROUND OF THE NEW PLANT

The present new variety "Blue Rosette" is a result of radiation treatments carried out in 1983 on meristimatic tissues of the cultivar "Blue Rococo," and appeared as a provoked mutant of Blue Rococo, grown as potted plants.

Asexual propagation of my new cultivar by cuttings in my greenhouse through several generations, has proved that the new cultivar is true to type, and constant in its characteristics. Descriptions were carried out on Nov. 12, 1985. Color readings were based on The Royal Horticultural Society's Colour Chart.

DESCRIPTION OF DRAWINGS

The new plant is illustrated in the accompanying drawings in which.

BRIEF SUMMARY

Figure 1:
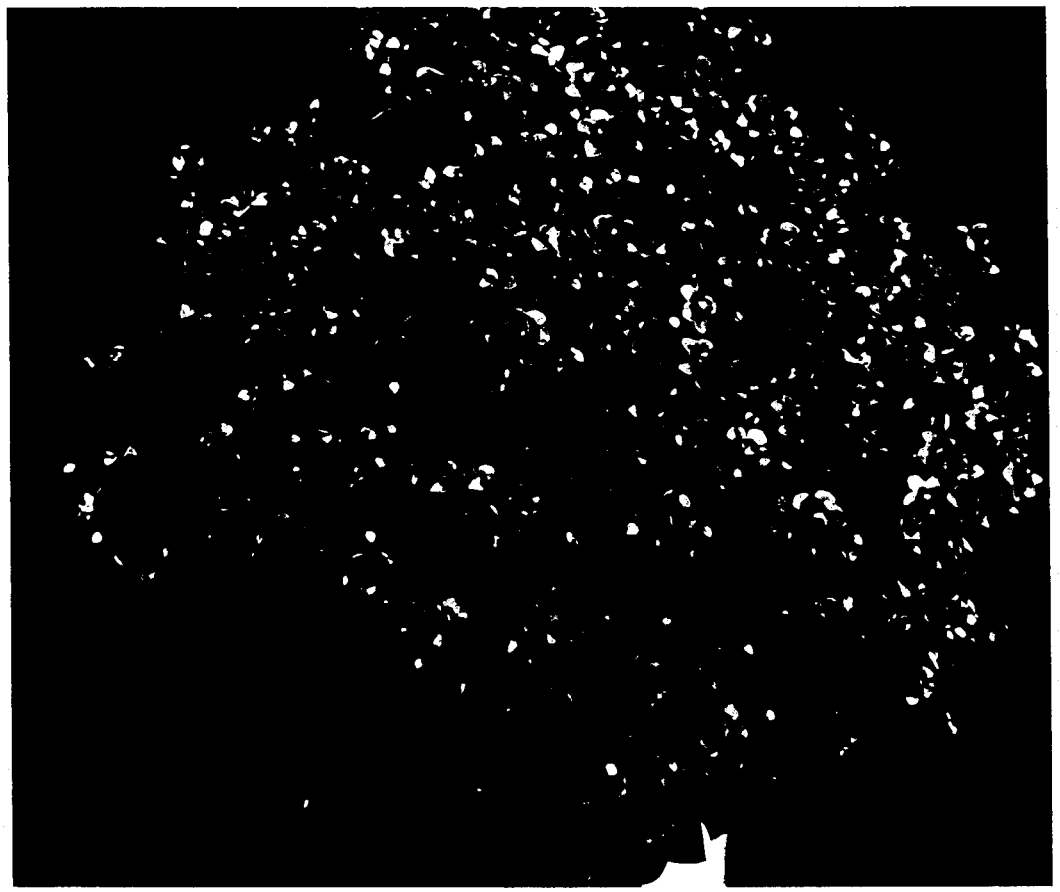
FIG. 1 is a full-color photograph of a potted plant in full bloom and FIG. 2 is a full-color photograph of the blossoms of the plant.
Figure 2:
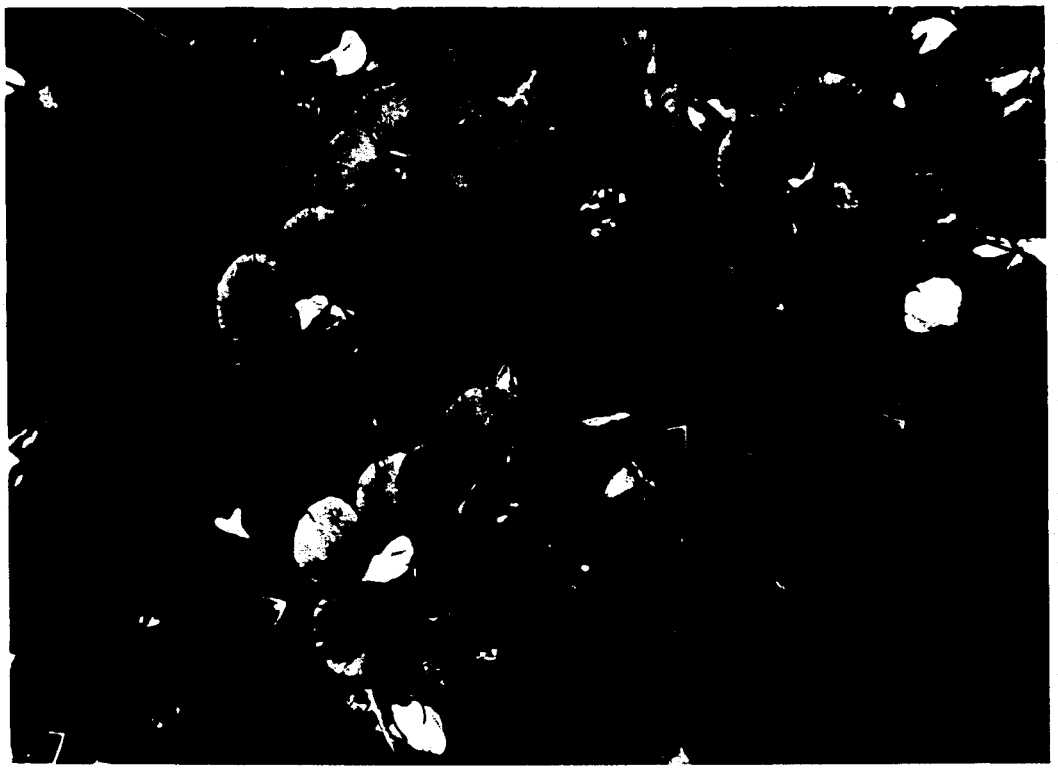

Exacum Affine Balf. "Blue Rosette" is a characteristic new mutant from an earlier variety of Blue Rococo and distinguishable from its origin as follows:

1. The flowers are semidouble.
2. Growth rate is equal to single-flowered seed-propagated cultivars.
3. Growth habit as potted plants is compact with an excellent branching ability.
4. Stamens are absent as they have become petalloid, forming a rosette in the flower center.
5. The flowers are sterile and produce no seed.
6. Reproduces easily with cuttings.
7. The keepability of the flower is slightly better than that for the single-flowered cultivars.

The accompanying color photograph illustrates the overall appearance of the cultivar "Blue Rosette." The flower color is slightly dependent on prevailing light conditions. The following is based on observations made on Nov. 12, 1985.

PLANT

Origin: Mutation in a well defined cultivar "Blue Rococo."
Form: Upright with heavy paniculate branching ability right from base to the terminal shoots.
Height: To flowering 18–25 cm.

Plant diameter: Similar to height.
Growth rate: Fast under good light conditions.
Type of cutting: Terminal shoots or stem segments.
Rooting time: 12–14 days.
Rooting habit: Dense and fibrous.

FOLIAGE

Arrangements: Oppositer sessile leaves at the bottom of all nodes.
Shape of leaves: Cordate to elliptic ovate.
Tip: Acute.
Base: Attenuate.
Margin: Entire.
Venation: Faintly three-veined from petiole. Middle vein strongest.
Size: Leaf-blade and petiole 40–60 mm. Length of blade 30–35 mm. Width at widest point 32–35 mm.
Surface: Slightly crinkled.
Texture: Glabrous.
Variegation: None.
Color:
*Petiole.*—144 B.
*Veins.*—145 B.
*Leaf surface.*—138 A, under side — 144 A.

STEM

Color: 144 B — at internodes purplish tinted.
Length of internodes: 25–32 mm.
Structure: Strong, rounded quadrangular.
Breaking action: Sympodial. One flower terminal at each node and two side shoots.

FLOWER

Form: Round.
Born: Terminal, single at the end of each node.
Bud: Round, 4–6 mm in diameter. Color 145 B.
Calyx: 5 winged. Color 143 B.
Petals: Five outer petals, each 7–8 mm wide forming a flat circular flower, 18–20 mm in diameter. In the center, 5 incurved petals of transformed stamens form a rosette. The number of petals depend on light conditions and day length. During the winter, some stamens are only partly petalloid.
Stamens: Normally absent.
Style: 12 mm long, white, with a yellowish stigma 2 mm above the central petals.
Petal color: 87B to 88B. Reverse side 86C.

Lasting quality: Average keepability one week depending on temperature.

Behaviour: The large number of flowers appear as an eye catcher at the surface of the compact green foliage, where new buds and flowers succeed the wilting.

Pedicels: 35–40 mm long, light purplish green.

Having thus disclosed my invention, I claim:

1. "Blue Rosette" to be a new and distinct cultivar of Exacum Affine as shown and described, characterized by its semidouble blue flowers, where the normal stamens are petalloid and arranged incurved as a rosette in the center of the lavender-blue-violet flower, by the sterility of the flower with the plants being propagated by asexual processes true to type, the excellent rooting ability, and the double flower differs from that of the other known cultivars.

* * * * *